United States Patent
Ruebben

(10) Patent No.: US 10,213,531 B2
(45) Date of Patent: *Feb. 26, 2019

(54) COATING OF A VASCULAR ENDOPROSTHESIS

(71) Applicant: AACHEN SCIENTIFIC INTERNATIONAL PTE. LTD., Singapore (SG)

(72) Inventor: Alexander Ruebben, Monaco (MC)

(73) Assignee: AACHEN SCIENTIFIC INTERNATIONAL PTE. LTD., Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 15/518,118

(22) PCT Filed: Oct. 9, 2015

(86) PCT No.: PCT/EP2015/073389
§ 371 (c)(1),
(2) Date: Apr. 10, 2017

(87) PCT Pub. No.: WO2016/055612
PCT Pub. Date: Apr. 14, 2016

(65) Prior Publication Data
US 2017/0360996 A1    Dec. 21, 2017

(30) Foreign Application Priority Data

Oct. 10, 2014 (DE) .................. 10 2014 014 774

(51) Int. Cl.
*B05D 3/10* (2006.01)
*A61L 31/10* (2006.01)
*A61L 31/16* (2006.01)

(52) U.S. Cl.
CPC ........... *A61L 31/10* (2013.01); *A61L 31/16* (2013.01); *A61L 2300/602* (2013.01); *A61L 2420/02* (2013.01)

(58) Field of Classification Search
CPC ..................................... B05D 3/107
USPC ........................... 427/2.28, 331, 337
See application file for complete search history.

(56) References Cited

U.S. PATENT DOCUMENTS

| 6,919,100 B2* | 7/2005 | Narayanan | A61L 31/10 427/2.1 |
| 2011/0092900 A1* | 4/2011 | Rubben | A61L 29/16 604/96.01 |
| 2011/0313514 A1* | 12/2011 | Omura | A61F 2/91 623/1.42 |
| 2015/0258311 A1* | 9/2015 | Rubben | A61L 29/085 604/103.02 |

FOREIGN PATENT DOCUMENTS

DE    102012010800 A1 *  12/2013  ........... A61L 29/085

* cited by examiner

*Primary Examiner* — Cachet I Sellman
(74) *Attorney, Agent, or Firm* — Raymond R. Ferrera; Adams and Reese LLP

(57) ABSTRACT

The invention concerns a method for coating a vascular endoprosthesis, wherein the vascular endoprosthesis is at least partially wetted with a first solution of an active ingredient and the areas of the vascular endoprosthesis at least partially wetted with the first solution of the active ingredient are at least partially wetted with a liquid containing water and/or at least an alcohol. The additional wetting with a liquid containing water/alcohol imparts a different consistency to the active ingredient layer, specifically making it is less transparent and lacquer-like and more chalklike and opaque. It has been found that such an active ingredient layer provides better transfer of the active ingredient to the blood vessels in which the vascular endoprosthesis is implanted.

26 Claims, No Drawings

COATING OF A VASCULAR ENDOPROSTHESIS

The invention concerns a method for coating a vascular endoprosthesis. The invention also concerns a vascular prothesis obtainable by said method.

So-called "minimally invasive methods" are becoming increasingly important in medicine. In treatment of vasoconstriction (stenosis), for example, vascular endoprostheses referred to as stents are frequently inserted into the vessel in order to keep it patent. The vascular endoprosthesis is typically tube-shaped and is composed of a braided or lattice structure of metal or plastic. In can take on a compressed form so that it can be inserted through a catheter to the target site. At the target site, the vascular endoprosthesis can then be dilated to its expanded shape. This expansion is carried out using a balloon. Self-expanding vascular endoprostheses, which are composed of a shape memory material and expand automatically as soon as they are no longer maintained in compressed form or are exposed to a change in temperature, are also known. The method of dilating blocked or stenosed blood vessels using a vascular endoprosthesis is also referred to as stent angioplasty.

It has been found to be problematic in use of conventional vascular endoprostheses that restenosis often occurs after a certain period due to cell proliferation and tissue neogenesis, i.e., the vascular lumen is again constricted. Drug-coated vascular endoprostheses (referred to as drug-eluting stents) are used in an attempt to prevent this. In particular, the drugs used for this purposes can be proliferation inhibitors such as paclitaxel or immunosuppressants such as sirolimus. The coating can be produced by applying the active ingredient to the vascular endoprosthesis dissolved in a solvent. In this way, the active ingredient is deposited on the vascular endoprosthesis and is gradually released following implantation.

Coating of a vascular endoprosthesis is typically carried out by bringing the vascular endoprosthesis into contact with a solution of the active ingredient, in which it is e.g. immersed. The solvent is then removed, for example by evaporation. It is also possible to precipitate the active ingredient by immersing the vascular endoprosthesis in a liquid, which mixes with the solvent of the active ingredient solution, but in which the active ingredient itself is largely insoluble. As a rule, this gives rise to a crystalline, lacquer-like coating of the vascular endoprosthesis. However, it has been found that in this type of vascular endoprosthesis, release of the active ingredient into the surrounding vascular wall after implantation is not always optimal.

Based on this prior art, the object is to provide a method for providing a vascular endoprosthesis that features improved release of the active ingredient.

This object is achieved according to the invention by means of a method for coating a vascular endoprosthesis comprising the following steps:
  a1) at least partial wetting of the vascular endoprosthesis with a first solution of an active ingredient, and
  b) at least partial wetting of the areas of the vascular prosthesis wetted with the first solution of the active ingredient with a liquid containing water and/or at least an alcohol.

It has been found that this wetting with the liquid containing water and/or at least an alcohol partially erodes the surface of the active ingredient and makes it more porous. This makes the coating more brittle, less optically transparent, and more opaque. The chalklike consistency of the surface results in greater erosion of the active ingredient and thus greater release of said active ingredient into surrounding vessels on insertion of the vascular endoprosthesis than would be the case without said wetting with the additional liquid containing water and/or at least an alcohol. The water or alcohol component is thought to cause a change in the crystalline structure of the active ingredient.

The step of wetting with the liquid containing water/alcohol should be carried out after the vascular endoprosthesis has been completely or largely dried and the active ingredient has crystallized out to the extent possible. The drying process may be supported by moving the vascular endoprosthesis and/or using an air or gas flow. The starting point for the additional wetting is thus a lacquer-like and transparent active ingredient layer that ensures homogenous and reproducible loading of the active ingredient. Wetting with the liquid containing water/alcohol is usually carried out by immersion, but other types of wetting such as spraying or dripping are also conceivable.

The liquid containing water and/or at least an alcohol should preferably be an aqueous solution containing an alcohol and/or ketone. The concentration of the alcohol and/or ketone in the aqueous solution is typically 10 to 70% (v/v), preferably 20 to 40% (v/v), and particularly preferably approx. 30% (v/v). In general, alcohols and ketones that are miscible with water may be used, with it also being possible to use a mixture of several alcohols and/or ketones, and all of the above-mentioned preferred concentrations are applicable in this case. The use of ethanol, methanol, acetone, and/or isopropanol is preferred. Ethanol is most preferable. The aqueous solution may also comprise an azeotropic solvent, particularly an alcohol/water mixture, and preferably an ethanol/water mixture. It is also possible to add a small amount, typically approx. 0.1% (v/v), of acetic acid, which stabilizes the active ingredient, in particular paclitaxel. After wetting, the vascular endoprosthesis is allowed to dry, preferably over a period of ≥2 min, more preferably ≥3 min, and particularly preferably ≥5 min. During this drying, the vascular endoprosthesis is preferably rotated and/or exposed to an air or gas flow in order to improve drying and remove excess solvent. Rotation may also be begun during wetting of the vascular endoprosthesis. It is also possible for the liquid to contain an additional amount of the active ingredient in order to further increase loading of the vascular endoprosthesis.

As typical vascular endoprostheses have a braided or lattice structure, and the circumference of the vascular endoprosthesis therefore has a plurality of openings, wetting of the vascular endoprosthesis with the solvent in which the active ingredient is dissolved is ordinarily carried out both internally and externally. However, this is also undesirable, because the active ingredient on the inner side of the vascular endoprosthesis also interferes with embedding of the vascular endoprosthesis in the endogenous tissue. According to a preferred embodiment, the method is therefore modified such that the interior of the vascular endoprosthesis remains largely free of the active ingredient. This is done by causing the vascular endoprosthesis in a step a2) to rotate rapidly about its longitudinal axis. Step a2) is carried out between steps a1) and b). The centrifugal force generated causes the solvent in which the active ingredient is dissolved to be spun outward, thus leaving the inner surface or inner area of the vascular endoprosthesis virtually free of the active ingredient. The vascular endoprosthesis may already be rotating during step a1), i.e. during wetting with the active ingredient solution. This applies in particular when the wetting is carried out by immersion in the corresponding solution. Alternatively, the vascular endoprosthesis may also be caused to rotate only after step a1) has been carried out.

The rotational speed should be at least 1,000 rpm, preferably at least 2,000 rpm, and particularly preferably at least 5,000 rpm. A rotational speed of 5,000 to 10,000 rpm has been found to be particularly advantageous. A correspondingly high rotational speed effectively ensures that the solvent containing the active ingredient is spun off and the inner area of the vascular endoprosthesis remains virtually free of the active ingredient. In addition, active ingredient residues that completely or partially span the interstices of the vascular endoprosthesis and extend into them are also removed. Such active ingredient residues are undesirable, because the amount of active ingredient contained therein is not reproducible or quantifiable. The vascular endoprosthesis is typically allowed to rotate over a period of 10 sec to 2 min after wetting with the active ingredient solution, and a period of 30 sec has generally been found to be sufficient. The rotation speed is considerably higher than in some methods known from prior art, in which movement is intended to achieve uniform distribution of the active ingredient or support drying.

As the interior of the vascular endoprosthesis remains largely free of the active ingredient, the vascular endoprosthesis is more rapidly covered with endothelium. Stimulation of blood coagulation by the vascular endoprosthesis is reduced to the same extent. By using the vascular endoprosthesis according to the invention, it is therefore possible to discontinue the use of anticoagulants such as acetylsalicylic acid at an earlier stage. At the same time, however, restenoses caused by application of the active ingredient to the outer side of the vascular endoprosthesis are effectively prevented.

Crystallization of the active ingredient on vascular endoprostheses has sometimes been found to be difficult. The reason is that unlike in the case of e.g. balloons for balloon angioplasty, the surface of the vascular endoprosthesis is hydrophilic rather than hydrophobic, with the result that crystallization nuclei of the typically hydrophobic active ingredients do not readily form on the surface of the vascular endoprosthesis.

According to a particularly preferred embodiment, in a step a3), a radially acting mechanical force is therefore exerted on the outside of the vascular endoprosthesis. This allows the active ingredient to crystallize well on the outer surface. Step a3) is carried out between steps a1) and b), or if step a2) is also carried out, between steps a2) and b).

In step a3), a radially acting mechanical force is exerted on the outer side of the vascular endoprosthesis, causing crystallization nuclei for the active ingredient to form, so that the (hydrophobic) active ingredient crystallizes well on the hydrophilic surface of the vascular endoprosthesis. It is important for this radially acting force to be exerted uniformly over the entire circumference on the outer side of the endoprosthesis in the areas in which wetting has been carried out. Radial force is understood to refer to a force that acts from outside over the circumference, in contrast to an axially-acting force on the longitudinal ends of the vascular endoprosthesis.

In particular, a radially acting mechanical force can be exerted by rolling the vascular endoprosthesis over a surface. This can be an elastomer surface such as a rubber surface. The pressure exerted on the vascular endoprosthesis should remain constant so that the force applied to the vascular endoprosthesis is uniform over its entire circumference. On rolling of the vascular endoprosthesis over the surface, crystallization nuclei are produced, which are important for the formation of a crystallized active ingredient coating. In order to avoid deformation during rolling over a surface, it is advisable to fill the inner space of the vascular endoprosthesis, for example with a rod preferably consisting of glass or metal.

Of course, alternative ways of exerting a radially acting mechanical force are also conceivable. For example, the vascular endoprosthesis can be inserted into a corresponding tool that is suitable for exerting a uniform, radially acting mechanical force. The force must be measured such that undesirable deformation of the vascular endoprosthesis does not occur.

Regardless of the manner in which force is exerted, whether by rolling over a surface or another method, a light pressure is typically sufficient, for example a force of 0.5 to 5 N, and preferably 1 to 3 N, e.g. 2 N.

The first solution may be saturated with respect to the active ingredient. Examples of suitable solvents include dichloromethane, chloroform, an alcohol, particularly ethanol, methanol, or isopropanol, acetone, diethyl ether, liquid hydrocarbons such as pentane, hexane, heptane, cyclohexane, or octane, toluene, tetrahydrofuran (THF), dimethylsulfoxide (DMSO), dioxane, dimethylformamide (DMF), or ethyl acetate. It is also possible to use solvent mixtures. A solution of the active ingredient in chloroform or dichloromethane is preferred, with chloroform being more preferable because it evaporates more slowly, thus allowing a longer period of time in which the solvent, together with the active ingredient, can be spun outward by the rotational movement.

A typical concentration of the active ingredient in the first solution is in the range of 50-500 mg/ml, and preferably 100-300 mg/ml. These concentrations have been found to be effective in forming a paclitaxel coating. In principle, a saturated solution of the active ingredient may also be used.

After wetting with the active ingredient solution, the vascular endoprosthesis is preferably removed from the first solution at a rate of ≤50 mm/sec, more preferably ≤40 mm/sec, more preferably ≤30 mm/sec, more preferably ≤20 mm/sec, more preferably ≤10 mm/sec, and even more preferably ≤5 mm/sec. Slow removal from the first solution allows uniform loading of the vascular endoprosthesis with an active ingredient layer. In addition, loading with the active ingredient can be controlled via the rate of removal.

It is also advisable to remove any impurities from the vascular endoprosthesis before carrying out step a1). This can be carried out either mechanically or by means of corresponding solvents, with cleaning with water, an alcohol, and/or a chlorinated organic solvent being particularly preferred. The alcohol should preferably be ethanol or isopropanol, and the chlorinated organic solvent should preferably be dichloromethane or chloroform. In particular, before wetting with the first solution containing the active ingredient, the vascular endoprosthesis may be immersed in a solvent not containing the active ingredient, which can also be used in the first solution, in order to first remove substances which would otherwise be released into the first solution. In addition, cleaning using a cloth moistened with solvent or the like is also possible.

In particular, the active ingredient used is a drug or medicinal product that has a proliferation-inhibiting action and prevents vasoconstrictive overgrowth of the site kept patent by the vascular endoprosthesis. In particular, the active ingredient can be selected form the following: tretinoin, orphan receptor agonists, elafin derivatives, corticosteroids, steroid hormones, paclitaxel, rapamycin, sirolimus, tacrolimus, hydrophobic proteins, and cell proliferation altering substances. It is also possible to use mixtures of these active ingredients. Moreover, derivatives of these active ingredients can also be used, with derivatives being understood in particular to refer to salts, esters, and amides. Examples of suitable steroid hormones include methylprednisolone, dexamethasone, and estradiol. The use of paclitaxel or paclitaxel derivatives is particularly preferred.

Coating of the vascular endoprosthesis with the active ingredient can also be carried out using solubilizing agents. Examples of known agents of this type include phosphatidyl choline, polyethoxyated castor oil, cardiolipin, cholesterol, and mixtures thereof. However, it is preferable not to use solubilizing agents.

The above-mentioned process steps, particularly step a1) and optionally a2), can also be repeated if necessary, i.e., an active ingredient dissolved in a solvent can be applied to the vascular endoprosthesis multiple times and removed from the interior of the vascular endoprosthesis by causing the prosthesis to rotate. This results in increased loading of the active ingredient. It is also conceivable to apply different active ingredients successively.

As a further step c) following the above-described step b), the areas of the vascular endoprosthesis wetted with the first solution and the liquid containing water and/or at least an alcohol can at least partially be wetted with an additional solution that contains a polysaccharide. Accordingly, the vascular endoprosthesis is (fully or partially) coated with a polysaccharide, with the polysaccharide coating being located on the outer side of the active ingredient, i.e. the active ingredient is largely coated with a polysaccharide layer. The polysaccharide coating can also be removed from inside the vascular endoprosthesis simply by wiping it off, because the polysaccharide in this case does not perform any function. As a rule, however, removal of the polysaccharide is not absolutely necessary, as the above-described process step a2) already sufficiently ensures that the interior of the vascular endoprosthesis remains virtually free of the active ingredient.

It has been found that the polysaccharide acts similarly to an adhesive on the inner wall of the treated vessel. i.e. the active ingredient shows considerably improved adhesion to the vascular wall and is more resistant to being entrained by the bloodstream. It is thought that the polysaccharide, which in contrast to the active ingredient is hydrophilic, readily swells in an aqueous environment such as blood, thus improving the transfer to the inner vascular wall. Accordingly, the active ingredient can exert its action over a long period of time, gradually being released from the polysaccharide coating and penetrating into the tissue of the vessel. It has been shown that even after approx. 3 months, significant concentrations of the active ingredient are still detectable. Without a polysaccharide coating, in contrast, virtually no active ingredient is present in the area of the inner vascular wall after 2 to 3 days, with the result that the protection provided by the active ingredient from the restenoses seen with conventional active ingredient-coated stents is no longer present after a relatively short period of time.

The improved fixation of the active ingredient on the endoprosthesis is to be seen as a further advantage of the polysaccharide coating. As the active ingredients such as paclitaxel used in coatings of vascular endoprostheses and exerting a proliferation-inhibiting action are often highly toxic, physicians and medical personnel must be protected from inhaling or touching these ingredients. Coating the active ingredient with a polysaccharide layer makes it possible to handle the vascular endoprosthesis without problems because the active ingredient is not released. The risk that users may inhale the active ingredient or absorb it through the skin is therefore minimized.

Because first the active ingredient, and then the polysaccharide as a polymer, are applied in dissolved form, this gives rise to uniform distribution of the polysaccharide around the active ingredient crystals of the existing active ingredient coating. In addition, hollow spaces between the active ingredient particles or in the surface of the vascular endoprosthesis are filled; the particles are coated with and encased in the polysaccharide.

In this connection, it is also particularly advantageous that the coating of the vascular endoprosthesis obtained in this manner is mechanically stable and flexible, which is important because a vascular endoprosthesis must often be passed via a catheter through narrow-lumen blood vessels to the target site. These properties also make packaging and handling of the vascular endoprosthesis safer.

Polysaccharides constitute a hydrophilic coating that undergoes a certain degree of swelling or softening in an aqueous environment. This causes the active ingredient to be favorably transferred to the inner wall of the vessel when the vascular endoprosthesis is expanded. The method according to the invention is particularly well-suited for lipophilic active ingredient coatings. Specifically, it has been found that hydrophilic polysaccharides in particular are well-suited for ensuring that lipophilic active ingredients are effectively transferred to the inner walls of the treated vessels during expansion of the vascular endoprosthesis, thus ensuring a lasting active ingredient concentration. It is assumed that in the method according to the invention, after the liquid containing water and/or at least an alcohol has caused the active ingredient to become brittle, the subsequently applied polysaccharide molecules are deposited between the water molecules, resulting in homogenous distribution of the active ingredient in the polysaccharide matrix. In vascular endoprostheses produced by the method according to the invention, the active ingredient is advantageously coated with the polysaccharide applied in the last step.

The polysaccharide is preferably present in an alcohol solution. In particular, in addition to one or more alcohols, this solution may also contain water. An aqueous alcohol solution is advantageous as it favorably dissolves the polysaccharide but does not remove the already-applied active ingredient layer. In addition, the organic component of the solution allows rapid drying after wetting. The concentration of the alcohol or alcohols in the aqueous alcohol solution is typically 10 to 70% (v/v), preferably 30 to 65% (v/v), more preferably 50 to 60% (v/v), and particularly preferably approx. 55% (v/v). Alcohols that dissolve the polysaccharide are also useable. As a rule, such alcohols are also miscible with water. Preferred are ethanol, methanol and isopropanol, with ethanol being particularly preferred. Following and/or during wetting with the solution containing a polysaccharide, the vascular endoprosthesis may in turn be caused to rotate or be rotating in order to remove excess solution and make drying faster.

Optionally, steps b) and c) may also be combined, because the aqueous alcohol solution in which the polysaccharide is dissolved is also suitable for producing the desired brittleness of the surface of the active ingredient. In this case, step b)/c) serves a simple purpose: on the one hand, the active ingredient layer becomes more porous, and on the other, the active ingredient layer is coated with the polysaccharide, with the polysaccharide also penetrating into the individual hollow spaces and interstices that form in the active ingredient layer.

A method including only steps a1) and c), i.e. in which step b) is omitted, is also to be considered part of the invention. A vascular endoprosthesis in which the active ingredient layer is covered with a polysaccharide layer is particularly advantageous with respect to the above-described aspects, even if the brittleness effect according to step b) is dispensed with. Accordingly, the invention also concerns a vascular endoprosthesis produced in this manner in which the active ingredient is at least partially coated with the polysaccharide. In addition, with respect to coating with the polysaccharide and the polysaccharide itself, the other embodiments according to the invention, as described in this application (with or without step b)) also apply.

The average molecular weight of the polysaccharide should preferably be 10,000 to 100,000,000 Da. An average molecular weight of 20,000 to 80,000 Da has been found to be particularly advantageous. Branched polysaccharides are preferred. The polysaccharide content of the additional solution should preferably be 1-15 wt %, more preferably 2-10 wt %, and particularly preferably 3-8 wt %.

The polysaccharide should preferably be a branched polysaccharide. Mixtures of several polysaccharides and modified polysaccharides are also suitable. Preferred are dextrans, particularly natural dextrans. Dextrans are high-molecular-weight branched polymers composed of glucose units. They are produced by bacteria such as those of the genus *Leuconostoc*. Dextrans are used as plasma expanders or as carriers in chromatography. They also have an anti-thrombogenic action.

The dextran should preferably be a natural dextran. Dextran 40, with an average molecular weight of approx. 40,000 Da, is particularly preferred.

In addition to dextrans, however, other polysaccharides can also ordinarily be used. An example of a suitable modified polysaccharide is hydroxyethyl starch (HES).

Wetting of the surface of the vascular endoprosthesis with any liquid (the first solution, the liquid containing water and/or at least an alcohol, or a further solution containing a polysaccharide) can be carried out by immersion in the liquid. As a rule, this immersion lasts a maximum of 1 min, and typically 10 to 30 sec, with a period of at least 50 sec being preferred for immersion in the liquid containing water/alcohol. Alternatively to wetting by immersion, wetting can also be carried out by another method such as spraying or dripping. After the individual wetting steps have been carried out, the surface of the vascular endoprosthesis is typically first allowed to dry before further process steps are carried out. Drying can be supported by exposure to an air or gas flow. Causing the vascular endoprosthesis to rotate also supports drying.

If necessary, the surface of the vascular endoprosthesis can be increased prior to application of the active ingredient by mechanical, chemical, or thermal means, e.g. by roughening or etching. This provides the surface with a coarser structure so that loading of the active ingredient can be increased. For example, the recesses in the surface produced in this manner can have a depth and a diameter of 5-50 μm.

All of the process steps can be carried out at room temperature.

In addition to the method according to the invention described above, the invention also concerns a vascular endoprosthesis, the outer side of which is at least partially covered with a coating of an active ingredient and which is obtainable by means of the method described above. The coating with the active ingredient and the polysaccharide may cover the entire outer surface of the vascular endoprosthesis or only partial areas thereof. It is important for the active ingredient layer to be made brittle by means of step b) in order to achieve greater abrasion and better transfer of the active ingredient to the vascular wall. It is also preferable to keep the inner area of the vascular endoprosthesis as free from the active ingredient as possible by causing the vascular endoprosthesis to rotate after coating with the active ingredient in order to allow endothelial growth thereon, which causes the vascular endoprosthesis to be embedded in the vessel. In this way, the vascular endoprosthesis is rapidly incorporated into the body tissue, and at the same time, the active ingredient present on the outer surface of the vascular endoprosthesis effectively prevents restenoses due to uncontrolled cell growth. For example, the vascular endoprosthesis according to the invention may be a stent such as those known for maintaining patency of a vascular lumen. Such a stent is typically tube-shaped and is composed of a braided or lattice structure of metal of plastic. The stent can take on a compressed form in order to insert it through a catheter to the target site. The stent is then dilated at the target site so that it assumes its expanded form.

It is particularly advantageous for the active ingredient also to be coated with a polysaccharide, particularly a dextran. This applies regardless of whether prior treatment with a liquid containing water/alcohol or the additional steps a2) and a3) described above have been carried out. The polysaccharide provides favorable adhesion of the active ingredient to the inner vascular wall so that the active ingredient is largely prevented from being entrained by the bloodstream. Accordingly, considerable concentrations of the active ingredient can be detected on the inner vascular wall even months later, while in conventional active ingredient-coated vascular endoprostheses, hardly any active ingredient is present on the inner vascular wall after a few days in some cases.

The invention claimed is:

1. A method for coating a vascular endoprosthesis, comprising the following steps:
    a1) at least partial wetting of the vascular endoprosthesis with a first solution of an active ingredient, and
    b) at least partial wetting of the areas of the vascular endoprosthesis wetted with the first solution solution of the active ingredient with a liquid containing one or more of a water and at least one of an alcohol and a ketone.

2. The method as claimed in claim 1, wherein the concentration of one or more of the alcohol and ketone in the liquid is between 10 and 70% (v/v).

3. The method as claimed in claim 1, wherein the liquid contains one or more of ethanol, methanol, acetone, and isopropanol.

4. The method as claimed in claim 1, wherein the vascular endoprosthesis, after wetting with the liquid containing one or more of water and at least one of an alcohol and a ketone, is dried for a period of ≥2 min.

5. The method as claimed in claim 1, comprising as a further step:
    a2) causing the vascular endoprosthesis to rotate about the longitudinal axis of the vascular endoprosthesis,
        wherein step a2) is carried out after step a1) and before step b).

6. The method as claimed in claim 5, wherein the vascular endoprosthesis is caused to rotate about the longitudinal axis at a rotational speed of at least 1,000 rpm.

7. The method as claimed in claim 5, wherein the vascular endoprosthesis is caused to rotate about the longitudinal axis at a rotational speed of at least 2,000 rpm.

8. The method as claimed in claim 5, wherein the vascular endoprosthesis is caused to rotate about the longitudinal axis at a rotational speed of at least 5,000 rpm.

9. The method as claimed in claim 1, comprising as a further step:
   a3) Exerting a radially acting mechanical force on the outer side of the vascular endoprosthesis,
   wherein step a3) is carried out after step a1) and before step b), or after step a2) and before step b).

10. The method as claimed in claim 9, wherein the radially acting mechanical force is exerted on the outside of the vascular endoprosthesis such that the vascular endoprosthesis is rolled over a surface while exerting pressure.

11. The method as claimed in claim 1, wherein the first solution further comprises chloroform or dichloromethane as a solvent.

12. The method as claimed in claim 1, wherein the vascular endoprosthesis is removed from the first solution at a rate of ≤50 mm/sec.

13. The method as claimed in claim 1, wherein the vascular endoprosthesis is cleaned using a solvent before the at least partial wetting of the vascular endoprosthesis with the first solution of the active ingredient, wherein one or more of water, an alcohol, and a chlorinated organic solvent is preferably used as a solvent.

14. The method as claimed in claim 1, comprising as a further step:
   c) at least partial wetting of the areas of the vascular endoprosthesis wetted with the first solution and the liquid containing one or more of water and at least one of an alcohol and a ketone with a further solution containing a polysaccharide,
   wherein step c) is carried out after step b).

15. The method as claimed in claim 14, wherein the average molecular weight of the polysaccharide is 10,000 to 100,000,000 Da.

16. The method as claimed in claim 14, wherein the polysaccharide is a dextran.

17. The method as claimed in claim 14, wherein the average molecular weight of the polysaccharide is 20,000 to 80,000 Da.

18. A method for coating a vascular endoprosthesis comprising the following steps:
   a1) at least partial wetting of the vascular endoprosthesis with a first solution of an active ingredient, and
   a2) at least partial wetting of the areas of the vascular endoprosthesis wetted with the first solution with a further solution containing a polysaccharide.

19. The method as claimed in claim 1, wherein the concentration of one or more of the alcohol and ketone in the liquid is 20 to 40% (v/v).

20. The method as claimed in claim 1, wherein the vascular endoprosthesis, after wetting with the liquid containing one or more of water and at least one of an alcohol and a ketone, is dried for a period of ≥3 min.

21. The method as claimed in claim 1, wherein the vascular endoprosthesis, after wetting with the liquid containing one or more of water and at least one of an alcohol and a ketone, is dried for a period of ≥5 min.

22. The method as claimed in claim 1, wherein the vascular endoprosthesis is removed from the first solution at a rate of ≤40 mm/sec.

23. The method as claimed in claim 1, wherein the vascular endoprosthesis is removed from the first solution at a rate of ≤30 mm/sec.

24. The method as claimed in claim 1, wherein the vascular endoprosthesis is removed from the first solution at a rate of ≤20 mm/sec.

25. The method as claimed in claim 1, wherein the vascular endoprosthesis is removed from the first solution at a rate of ≤10 mm/sec.

26. The method as claimed in claim 1, wherein the vascular endoprosthesis is removed from the first solution at a rate of ≤5 mm/sec.

* * * * *

UNITED STATES PATENT AND TRADEMARK OFFICE
CERTIFICATE OF CORRECTION

PATENT NO. : 10,213,531 B2
APPLICATION NO. : 15/518118
DATED : February 26, 2019
INVENTOR(S) : Alexander Ruebben Page 1 of 1

It is certified that error appears in the above-identified patent and that said Letters Patent is hereby corrected as shown below:

On the Title Page

Under Foreign Application Priority Data: "10 2014 014 774" should read -- 10 2014 014 771 --.

Signed and Sealed this
Thirtieth Day of July, 2019

Andrei Iancu
*Director of the United States Patent and Trademark Office*